(12) United States Patent
Gregerson et al.

(10) Patent No.: US 7,188,998 B2
(45) Date of Patent: Mar. 13, 2007

(54) SYSTEMS AND METHODS FOR QUASI-SIMULTANEOUS MULTI-PLANAR X-RAY IMAGING

(75) Inventors: Eugene A. Gregerson, Bolton, MA (US); Richard K. Grant, Sudbury, MA (US); Norbert Johnson, North Andover, MA (US)

(73) Assignee: Breakaway Imaging, LLC, Littleton, MA (US)

( * ) Notice: Subject to any disclaimer, the term of this patent is extended or adjusted under 35 U.S.C. 154(b) by 0 days.

(21) Appl. No.: 10/389,268

(22) Filed: Mar. 13, 2003

(65) Prior Publication Data

US 2004/0013239 A1    Jan. 22, 2004

Related U.S. Application Data

(60) Provisional application No. 60/363,902, filed on Mar. 13, 2002.

(51) Int. Cl.
*H05G 1/04* (2006.01)
(52) U.S. Cl. .......................................... 378/197; 378/62
(58) Field of Classification Search ................. 378/62, 378/193–197, 198, 37, 51, 10, 4–20, 57, 378/21, 102
See application file for complete search history.

(56) References Cited

U.S. PATENT DOCUMENTS

| 3,549,885 A | 12/1970 | Andersson |
| 3,617,749 A | 11/1971 | Massiot |
| 4,200,799 A | 4/1980 | Saito |

(Continued)

FOREIGN PATENT DOCUMENTS

DE    G 89 05 588.8    9/1990

(Continued)

OTHER PUBLICATIONS

Siremobil Iso-C$^{3D}$ Breathtaking Views in the OR!, SIEMENS, Siemens Aktiengesellschaft Medical Solutions Henkestrasse 127, D-91052 Erlangen, pp. 1-16, no date given.

(Continued)

*Primary Examiner*—Edward J. Glick
*Assistant Examiner*—Hoon Song
(74) *Attorney, Agent, or Firm*—Hamilton, Brook, Smith & Reynolds, P.C.

(57) ABSTRACT

Systems and methods for obtaining two-dimensional images of an object, such as a patient, in multiple projection planes. In one aspect, the invention advantageously permits quasi-simultaneous image acquisition from multiple projection planes using a single radiation source.

An imaging apparatus comprises a gantry having a central opening for positioning an object to be imaged, a source of radiation that is rotatable around the interior of the gantry ring and which is adapted to project radiation onto said object from a plurality of different projection angles; and a detector system adapted to detect the radiation at each projection angle to acquire object images from multiple projection planes in a quasi-simultaneous manner. The gantry can be a substantially "O-shaped" ring, with the source rotatable 360 degrees around the interior of the ring. The source can be an x-ray source, and the imaging apparatus can be used for medical x-ray imaging. The detector array can be a two-dimensional detector, preferably a digital detector.

33 Claims, 12 Drawing Sheets

U.S. PATENT DOCUMENTS

| | | | |
|---|---|---|---|
| 4,352,986 A | 10/1982 | Pfeiler | |
| 4,442,489 A | 4/1984 | Wagner | |
| 4,481,656 A | 11/1984 | Janssen et al. | |
| 4,741,015 A * | 4/1988 | Charrier | 378/196 |
| 4,803,714 A | 2/1989 | Vlasbloem | |
| 4,810,881 A | 3/1989 | Berger et al. | |
| 4,829,252 A | 5/1989 | Kaufman | |
| 4,875,228 A | 10/1989 | Archer | |
| 4,884,293 A | 11/1989 | Koyama | |
| 4,935,949 A * | 6/1990 | Fujita et al. | 378/198 |
| 4,955,046 A | 9/1990 | Siczek et al. | |
| 4,982,415 A * | 1/1991 | Shibata et al. | 378/15 |
| 4,987,585 A | 1/1991 | Kidd et al. | |
| 5,014,292 A | 5/1991 | Siczek et al. | |
| 5,014,293 A | 5/1991 | Boyd et al. | |
| 5,032,990 A | 7/1991 | Eberhard et al. | |
| D323,386 S | 1/1992 | Perusek | |
| 5,084,908 A | 1/1992 | Alberici et al. | |
| 5,095,501 A | 3/1992 | Kobayashi | |
| 5,097,497 A | 3/1992 | Deucher et al. | |
| 5,159,622 A | 10/1992 | Sakaniwa et al. | |
| 5,187,659 A | 2/1993 | Eberhard et al. | |
| 5,265,610 A | 11/1993 | Darrow et al. | |
| 5,287,274 A | 2/1994 | Saint Felix et al. | |
| D345,606 S | 3/1994 | Perusek | |
| 5,319,693 A | 6/1994 | Eberhard et al. | |
| 5,390,112 A | 2/1995 | Tam | |
| 5,448,607 A | 9/1995 | McKenna | |
| 5,448,608 A | 9/1995 | Swain et al. | |
| 5,452,337 A | 9/1995 | Endo et al. | |
| 5,499,415 A | 3/1996 | McKenna | |
| 5,515,416 A | 5/1996 | Siczek et al. | |
| 5,583,909 A | 12/1996 | Hanover | |
| 5,592,523 A | 1/1997 | Tuy et al. | |
| 5,598,453 A * | 1/1997 | Baba et al. | 378/146 |
| 5,625,660 A | 4/1997 | Tuy | |
| 5,638,419 A | 6/1997 | Ingwersen | |
| 5,661,772 A | 8/1997 | Bär et al. | |
| 5,740,222 A | 4/1998 | Fujita et al. | |
| 5,740,224 A | 4/1998 | Müller et al. | |
| 5,745,545 A | 4/1998 | Hughes | |
| 5,784,428 A | 7/1998 | Schmidt | |
| 5,802,138 A | 9/1998 | Glasser et al. | |
| 5,912,943 A | 6/1999 | Deucher et al. | |
| RE36,415 E | 11/1999 | McKenna | |
| 6,041,097 A | 3/2000 | Roos et al. | |
| 6,147,352 A | 11/2000 | Ashburn | |
| 6,203,196 B1 | 3/2001 | Meyer et al. | |
| 6,212,251 B1 * | 4/2001 | Tomura et al. | 378/15 |
| 6,289,073 B1 | 9/2001 | Sasaki et al. | |
| 6,314,157 B1 * | 11/2001 | Tachizaki | 378/4 |
| 6,322,251 B1 | 11/2001 | Ballhaus et al. | |
| 6,324,246 B1 | 11/2001 | Ruimi | |
| 6,325,537 B1 | 12/2001 | Watanabe | |
| 6,442,235 B2 * | 8/2002 | Koppe et al. | 378/82 |
| 6,484,049 B1 | 11/2002 | Seeley et al. | |
| 6,487,267 B1 | 11/2002 | Wolter | |
| 6,496,558 B2 | 12/2002 | Graumann | |
| 6,519,312 B1 | 2/2003 | Tybinkowski et al. | |
| 6,546,068 B1 | 4/2003 | Shimura | |
| 6,609,826 B1 | 8/2003 | Fujii et al. | |
| 2001/0005410 A1 | 6/2001 | Rasche et al. | |
| 2002/0031201 A1 * | 3/2002 | Suzuki et al. | 378/4 |
| 2002/0118793 A1 | 8/2002 | Horbaschek | |
| 2002/0168053 A1 | 11/2002 | Schomberg | |
| 2003/0072416 A1 | 4/2003 | Rasche et al. | |

FOREIGN PATENT DOCUMENTS

| | | |
|---|---|---|
| DE | 195 35 583 A1 | 3/1997 |
| DE | 198 39 825 C 1 | 10/1999 |
| DE | 199 27 953 A1 | 1/2001 |
| EP | 0 471 455 A2 | 7/1991 |
| EP | 0 564 292 A2 | 6/1993 |
| EP | 0 564 292 | 10/1993 |
| EP | 0 810 005 A2 | 12/1997 |
| EP | 1 090 585 A1 | 4/2001 |
| FR | 2 304 321 | 10/1976 |
| GB | 2 088 670 A | 6/1982 |
| WO | WO 96/06561 | 3/1996 |

OTHER PUBLICATIONS

Ning, R., et al., "An Image Intensifier-Based Volume Tomographic Angiography Imaging System", *SPIE* vol. 3032, pp. 238-247.

Chabbal, J., et al., "Amorphous Silicon X-Ray Image Sensor", *Physics of Medical Imaging*, Proceedings of SPIE, Feb. 23-25, 1997, vol. 3032.

Hsuing, H., et al., "3D x-ray angiography: Study of factors affecting projection data consistency", *Physics of Medical Imaging*, Proceedings of SPIE, pp. 226-237, Feb. 23-25, 1997, vol. 3032.

Lwata, K., et al., "Description of a Prototype Combined CT-SPECT System with a Single CdZnTE Dector", *Nuclear Science Symposium Conference Record*, 2000 IEEE, XP010556613, pp. 16-1-16-5.

Lang, T.F., et al., "A Prototype Emission-Transmission Imaging System", *Proceedings of the Nuclear Science Symposium and Medical Imaging Conference*, 1991 IEEE, XP010058199, pp. 1902-1906.

Lang, Thomas, F., et al., "Description of a Prototype Emission—Transmission Computed Tomography Imaging System", *Journal of Nuclear Medicine, Society of Nuclear Medicine*, 1992, XP002901050, pp. 1881-1887.

* cited by examiner

FIG. 1

AP Position
FIG. 2A

Lateral Position
FIG. 2B

AP Position
FIG. 2C

Lateral Position
FIG. 2D

Rotor Angle (0°)

FIG. 6A

Rotor Angle (90°)

FIG. 6B

FIG. 6C   Rotor Angle (180°)

Rotor Angle (270°)

FIG. 6D

Rotor Angle (360°)

SYSTEMS AND METHODS FOR QUASI-SIMULTANEOUS MULTI-PLANAR X-RAY IMAGING

RELATED APPLICATION

This application claims the benefit of U.S. Provisional Application No. 60/363,902, filed Mar. 13, 2002, the entire teachings of which are incorporated herein by reference.

BACKGROUND OF THE INVENTION

It is often desirable to take x-rays of a patient from a number of different positions, preferably without the need for frequent manual repositioning of the patient of the x-ray system. Mobile C-arm x-ray diagnostic equipment has been developed for this purpose, and has become well known in the medical art of surgical and other interventional procedures.

A C-arm refers generally to an elongated C-shaped member terminating in opposing distal ends of the "C" shape. An x-ray source and an image receptor are typically mounted at or near the distal ends, respectively, of the C-arm in opposing orientation, with the C-arm supported in a suspended position. The space within the C-shape of the arm provides room for the physician to attend to the patient substantially free of interference from the x-ray support structure. The support structure usually rests upon wheels, which enable the C-arm to be wheeled from room to room, also to move along the length of a patient while the physician operates or examines. The x-ray images from such devices are often used in the operating room environment to help ensure that devices such as surgical instrumentation are properly positioned during the procedure.

The C-arm is usually mounted so as to enable rotational movement of the arm in two degrees of freedom, i.e. about two perpendicular axes in a spherical motion. More specifically, the C-arm is slidably mounted to the support structure to enable orbiting rotational movement of the C-arm about its center of curvature, thereby permitting selective orientation of the x-ray source and the image receptor vertically, horizontally, or somewhere in between. The C-arm is also laterally rotatable, i.e. in a perpendicular direction relative to the orbiting direction to enable selectively adjustable positioning of the x-ray source and receptor relative to both the width and length of the patient. The spherically rotational aspects of C-arm apparatus allows the physician to take x-rays of the patient at an optimal angle as determined with respect to the particular anatomical condition being imaged. An example of such a C-arm apparatus is described in U.S. Pat. No. 4,955,046 to Siczek, et al., which discloses a C-arm apparatus on a wheeled support cart.

In many cases, it is desirable to obtain x-ray images of a patient from multiple projection planes, preferably in quick succession and without repositioning the C-arm. Such a configuration is often referred to as bi-planar imaging and allows an object to be viewed in two planes simultaneously. The two x-ray beams emitted from the two x-ray tubes may cross at an iso-center. Bi-planar imaging is useful for checking of a catheter position, a balloon status or performing a digital subtraction run.

Bi-planar imaging may be accomplished in several ways. One way is by using two independent imaging systems, or two C-arms. U.S. Pat. No. 4,884,293 to Koyama discusses a dual imaging system with one imaging system being mounted to the floor and the other being mounted to the ceiling. One disadvantage of this system is that it is permanently mounted to the floor and ceiling. Thus, the system cannot be moved about a hospital as needed. Another disadvantage of this system is that, although the C-arms are coordinated, the imaging systems operate independently of one another. Thus, the images produced are not coordinated.

Another configuration for obtaining bi-planar imaging is slidingly nesting one C-arm in another. U.S. Pat. No. 5,515,416 to Siczek et al. describes a dual imaging system with one C-arm being mounted to the floor and the other C-arm being slidingly disposed on the first C-arm. One disadvantage of this system is that the two imaging systems may not be moved independently of one another. Thus, the positioning of the second imaging system is limited by the position of the first. Another disadvantage is that the dual x-ray system is permanently mounted to the floor. Thus, it cannot be moved about a hospital. A further disadvantage is that the two images must share a common iso-center because they are nested.

Yet another configuration for obtaining bi-planar imaging is disposing the imaging systems in a ring, as opposed to C-arms. U.S. Pat. No. 3,549,885 to Andersson discloses a dual imaging system with both imaging systems being mounted perpendicularly in a rotatable ring. One disadvantage with this system is that the bi-planar images are always disposed at a fixed, perpendicular angle with respect to each other.

Still another configuration for obtaining bi-planar imaging is disposing the imaging systems on a G-arm, as opposed to C-arms. U.S. Pat. No. 5,095,501 to Kobayashi discloses a dual imaging system with both imaging systems being mounted perpendicularly in a G-shaped arm. Like the ring configuration above, one disadvantage of this system is that the bi-planar images are always disposed at a fixed, perpendicular angle with respect to each other.

Furthermore, it is often desirable to view x-rays in real time and to save or store x-rays taken of a patient for later review. Dual imaging systems are complicated and difficult to operate because they require simultaneous coordination and operation of two independent and distinct imaging systems. In addition, if both imaging systems operate at the same time, the two x-ray beams interact to cause a blurred image. Moreover, the use of two x-ray sources can result in exposure of the subject to excessive radiation, particularly due to scattering effects. To date, there does not exist an electromagnetic radiation imaging system that employs a single source to provide simultaneous or near-simultaneous acquisition of object images from multiple projection planes.

SUMMARY OF THE INVENTION

The present invention relates to systems and methods for obtaining two-dimensional images of an object, such as a patient, in multiple projection planes. In one aspect, the invention advantageously permits quasi-simultaneous image acquisition from multiple projection planes using a single radiation source.

An imaging apparatus comprises a gantry having a central opening for positioning around an object to be imaged, a source of radiation that is rotatable around the interior of the gantry and which is adapted to project radiation onto said object from a plurality of different projection angles; and a detector system adapted to detect the radiation at each projection angle to acquire object images from multiple projection planes in a quasi-simultaneous manner. As used herein, the term "quasi-simultaneous" means that there is no appreciable delay between the acquisition of the object images, beyond the time it takes for the source to rotate between different projection angles. In a preferred embodiment, the gantry is a substantially "O-shaped" ring, and the source is rotatable 360 degrees around the interior of the ring. The source can be an x-ray source, and the imaging apparatus can be used for medical x-ray imaging.

In certain embodiments, the gantry is attached to a support structure, such as a mobile cart, in a cantilevered fashion. A positioning unit can translate and/or tilt the gantry to a desired position and orientation, preferably under control of a computerized motion control system. The gantry can include a source and detector disposed opposite one another on the gantry. The source and detector can be secured to a motorized rotor, which rotates the source and detector around the interior of the gantry in coordination with one another. The source can be pulsed at multiple positions and orientations over a partial or full 360-degree rotation for multi-planar imaging of a targeted object located inside the gantry. The gantry can further include a rail and bearing system for guiding the rotor as it rotates, carrying the source and detector.

The invention also relates to a method of obtaining quasi-simultaneous multi-planar object images using radiation, comprising positioning an object within a central opening of a gantry; rotating a radiation source within the gantry to a plurality of projection angles; at each projection angle, projecting radiation from the source onto the object; and detecting radiation from the object at each projection angle to acquire object images for multiple projection planes in a quasi-simultaneous manner. Preferably, the source is an x-ray source, and the detected x-ray radiation can be used to produce multi-planar two-dimensional x-ray object images.

The invention advantageously enables quasi-simultaneous multi-planar imaging, including collection and updating of AP (anterior/postior), lateral, oblique, and cinematic views of a patient or targeted object throughout a partial or full 360-degree rotation, which can be accomplished with a single x-ray source and a single two-dimensional detector array.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
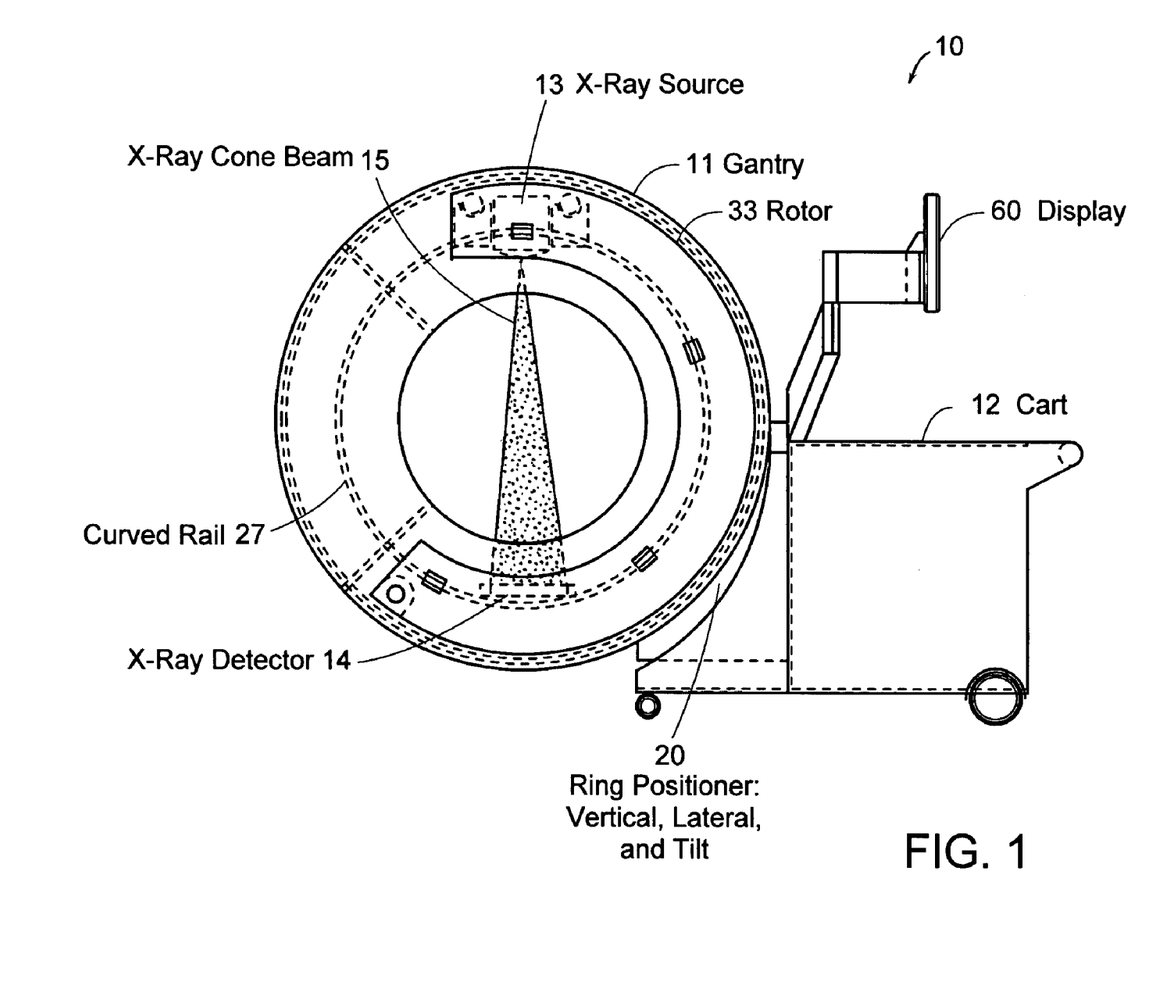
FIG. 1 is a schematic diagram showing an x-ray scanning system according to one embodiment of the invention.

FIG. 1 is a schematic diagram showing an x-ray scanning system 10 in accordance with one embodiment of the invention. The x-ray scanning system 10 includes a gantry 11 secured to a support structure, which could be a mobile or stationary cart, a patient table, a wall, a floor, or a ceiling. As shown in FIG. 1, the gantry 11 is secured to a mobile cart 12 in a cantilevered fashion via a ring positioning unit 20. In certain embodiments, the ring positioning unit 20 translates and/or tilts the gantry 11 with respect to the support structure to position the gantry 11 in any number of imaging positions and orientations.

The mobile cart 12 of FIG. 1 can optionally include a power supply, an x-ray power generator, and a computer system for controlling operation of the x-ray scanning device and for performing image processing, storage of x-ray images, or other data processing functions. In a preferred embodiment, the computer system controls the positioning unit 20 to enable the gantry 11 to be quickly moved to a particular user-defined position and orientation. The computer preferably has a memory that is capable of storing positioning information relating to particular gantry positions and/or orientations. This stored positioning information can be used to automatically move the gantry to a pre-defined configuration upon demand.

The mobile cart 12 preferably also includes a display system 60, such as a flat panel display, for displaying images obtained by the x-ray scanner. The display can also include a user interface function, such as a touch-screen controller, that enables a user to interact with and control the functions of the scanning system. In certain embodiments, a user-controlled pendant or foot pedal can control the functions of the scanning system.

It will be understood that one or more fixed units can also perform any of the functions of the mobile cart 12.

According to one aspect, the x-ray scanning system of the invention can be used to obtain two-dimensional x-ray images of an object, such as a patient, in multiple projection planes. In the embodiment shown in FIG. 1, the gantry 11 is a generally circular, or "O-shaped," housing having a central opening into which an object being imaged is placed. The gantry 11 contains an x-ray source 13 (such as a rotating anode pulsed x-ray source) that projects a beam of x-ray radiation 15 into the central opening of the gantry, through the object being imaged, and onto a detector array 14 (such as a flat panel digital detector array) located on the opposite side of the gantry. The x-rays received at the detector 14 can then be used to produce a two-dimensional image of the object using well-known techniques.

The x-ray source 13 is able to rotate around the interior of the gantry 111 in a continuous or step-wise manner so that the x-ray beam can be projected through the object, and through a common isocenter, at various angles over a partial or full 360 degree rotation. The detector array is also rotated around the interior of the gantry, in coordination with the rotation of the x-ray source, so that for each projection angle of the x-ray source, the detector array is positioned opposite the x-ray source on the gantry. The apparatus is thus able to obtain two-dimensional x-ray images of the targeted object in any projection plane over a partial or full 360 degree rotation.

Figure 2A:
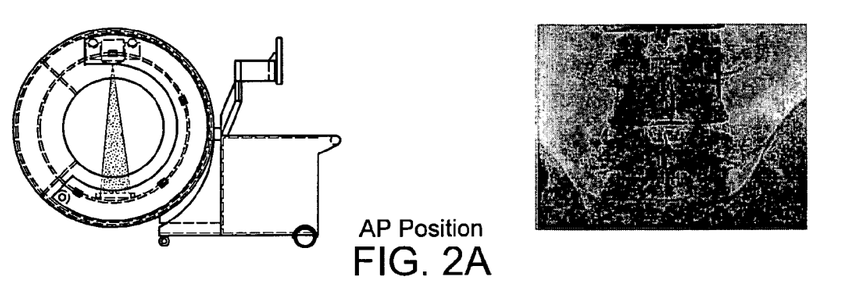
FIGS. 2A–2D show the x-ray scanning system of FIG. 1 acquiring quasi-simultaneous anterior/posterior and lateral images of a spine throughout a rotation of a motorized rotor within the O-shaped x-ray gantry.
Figure 11:
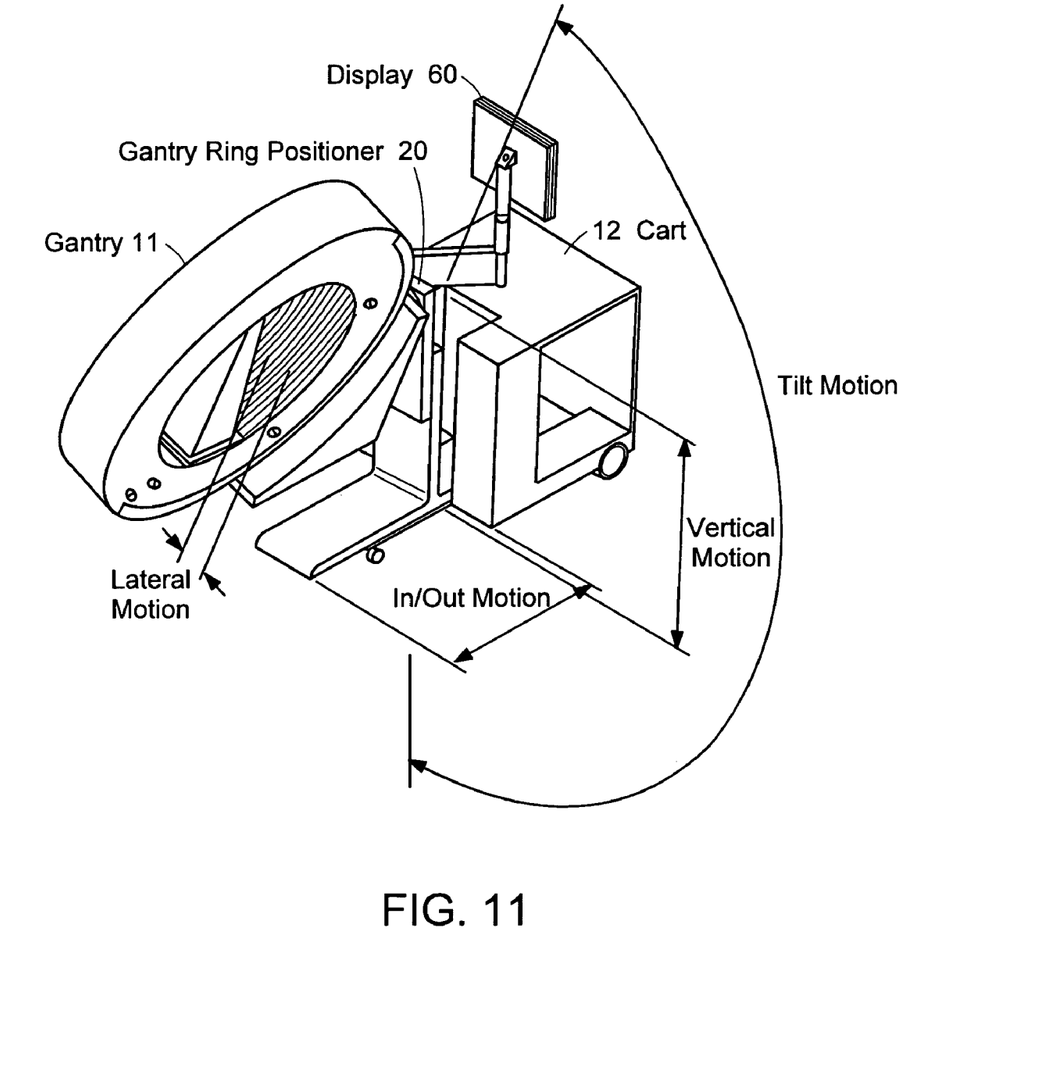
FIG. 11 shows the gantry ring and positioning unit in fully extended lateral, vertical, and tilt positions.

The x-ray system of the invention can be operated in a static or in a multi-planar mode. In a static mode, a user selects a desired imaging plane in the target object, and the x-ray source and detector are rotated to the appropriate angle within the gantry. As shown in FIG. 2A, for example, the x-ray source and detector are at the top and bottom of the gantry, respectively, for acquisition of an anterior-posterior (AP) type patient image. Alternatively, or in addition, the gantry itself can be moved by positioning or tilting the gantry relative to the target object using the gantry positioning unit 20, as shown in FIG. 11. In static mode, the x-ray scanner can acquire and display a single x-ray image of the object, or can obtain multiple images of the object, and continuously update the display with the most recent image. In a preferred embodiment, the x-ray scanner obtains multiple object images in quick succession, and displays these images in real time (e.g. 30 frames per second) in a "cinematic" mode.

Figure 2B:
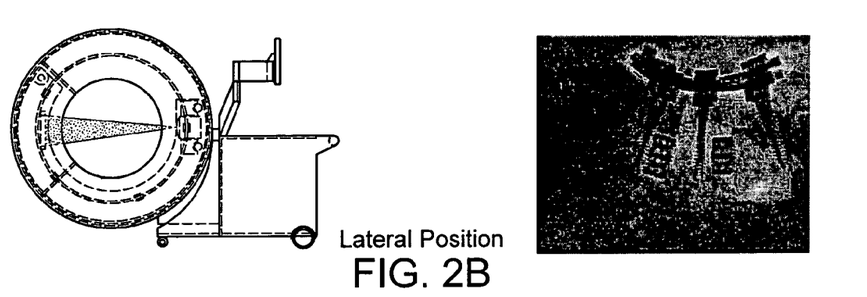
Figure 2C:
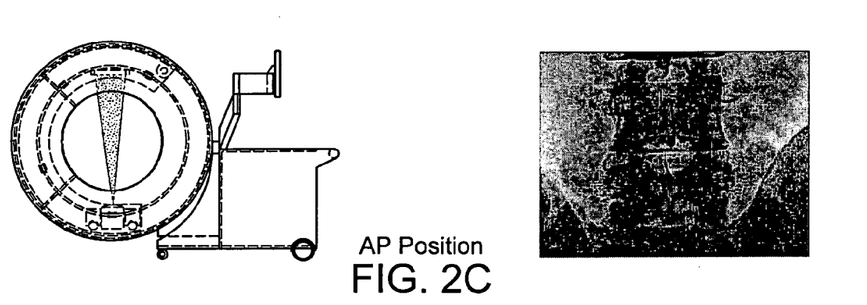
Figure 2D:
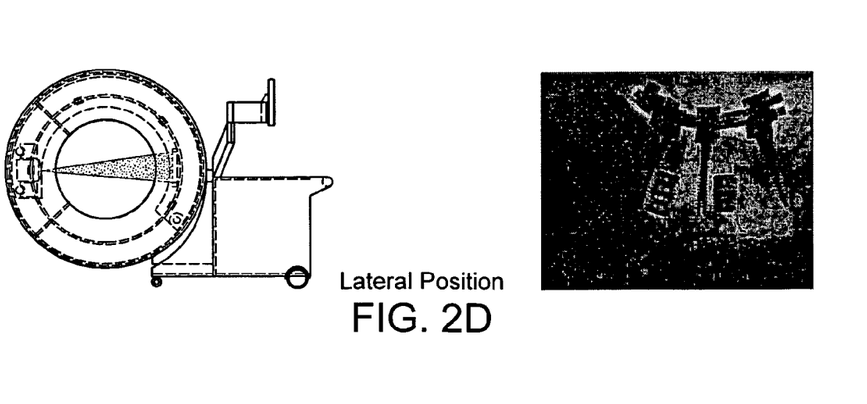

To change the imaging plane of the object, the x-ray source and detector can be rotated to another angle within the gantry. As shown in FIG. 2B, for example, the source and detector rotate 90 degrees in a clockwise direction for obtaining object images in a lateral plane. Alternatively or in addition, translating or tilting the entire gantry to a second position can change the imaging plane.

In multi-planar mode, the x-ray scanner obtains a series of images from multiple projection planes in rapid succession. The imaging system advantageously permits quasi-simultaneous multi-planar imaging using a single radiation source. As shown in FIG. 2A, for example, the x-ray source 13 and detector 14 are initially positioned at the top and bottom of the gantry respectively and acquire a first x-ray image of the target object, which in this case is an anterior-posterior (AP) view of a patient's spine. The source and detector then rotate 90 degrees clockwise within the fixed gantry to obtain a second x-ray image shown in FIG. 2B, which is a lateral view of the spine. These bi-planar AP/lateral images are obtained quasi-simultaneously, as there is no appreciable delay between the acquisition of the two images, other than the time it takes for the source to rotate between projection angles on the gantry. Additional AP/lateral images can be obtained and continuously updated by alternatively rotating the source and detector between two projection angles, such as the two perpendicular projections shown FIGS. 2A and 2B. In a preferred embodiment, however, quasi-simultaneous multi-planar images are obtained and updated in real time by continuously rotating the source and detector over a full 360 degree rotation, obtaining images at desired rotational increments. As shown in FIGS. 2A–2B, for example, four bi-planar images, including two AP images, and two lateral images, can be obtained in quick succession during a single 360 degree rotation of the source and detector. These images can be displayed individually, sequentially, side-by-side, or in any desired manner.

Figure 3:
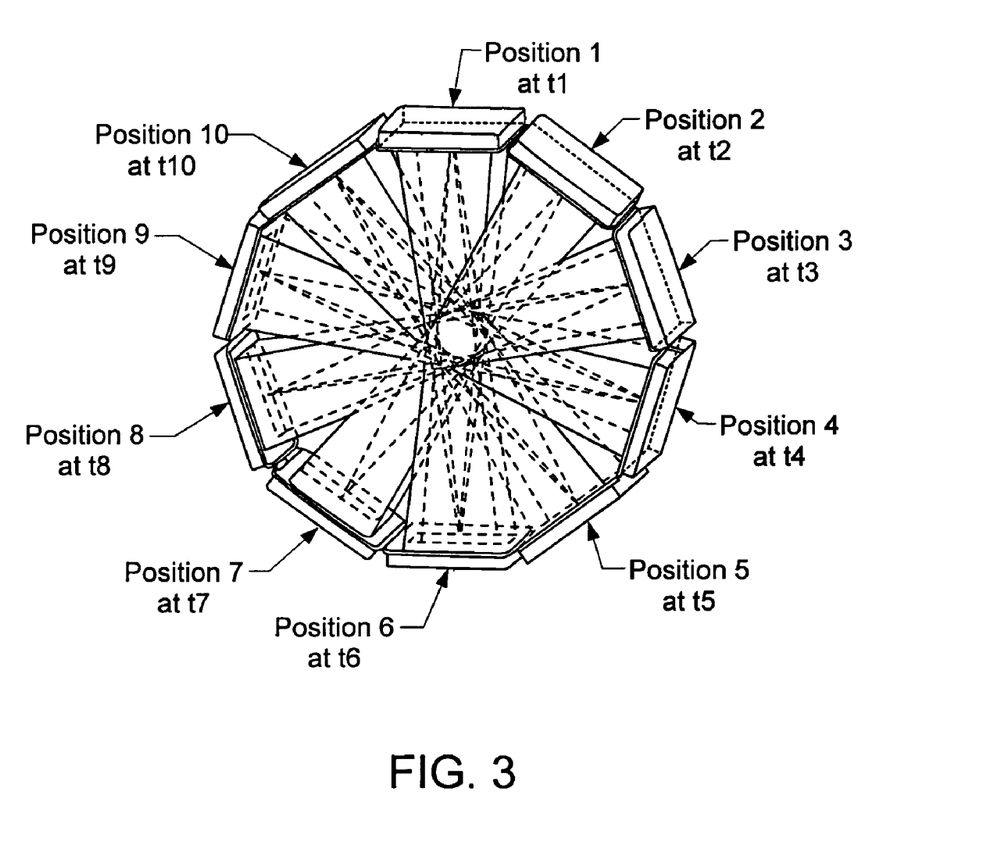
FIG. 3 shows an x-ray detector array capturing multiple x-ray images throughout a 360 degree rotation.

A further illustration of the quasi-simultaneous multi-planar imaging of the invention is shown in FIG. 3. Here, a rotatable detector array is shown capturing quasi-simultaneous x-ray images of ten incremental projection planes over a full 360 degree rotation. These images are captured continuously, or in a step wise fashion. They can be displayed individually, side-by-side, sequentially in a cinematic mode, or in any desired manner.

Figure 4:
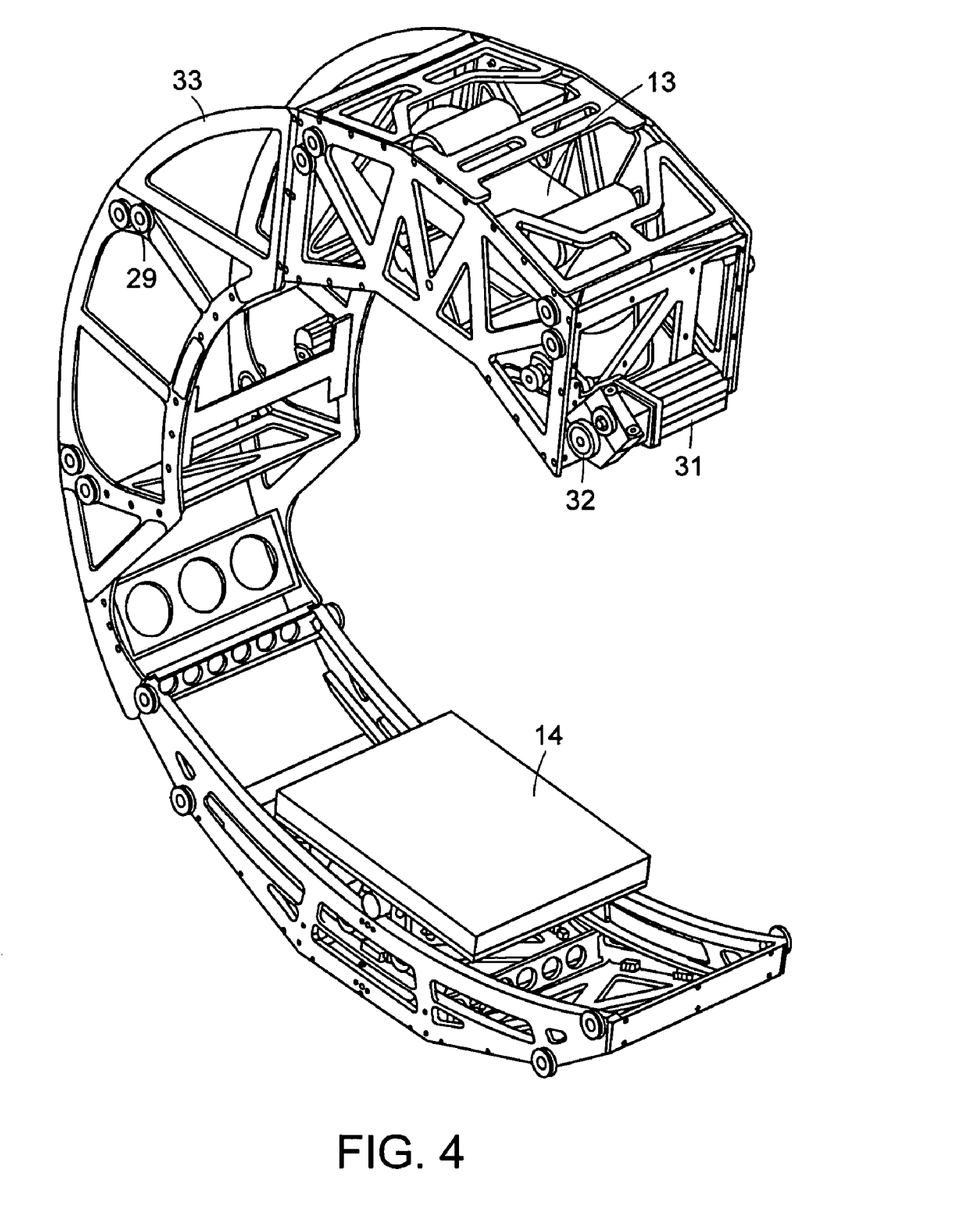
FIG. 4 illustrates a motorized rotor assembly for rotating an x-ray source and detector array within the gantry ring of an x-ray scanning device of the invention.
Figure 5A:
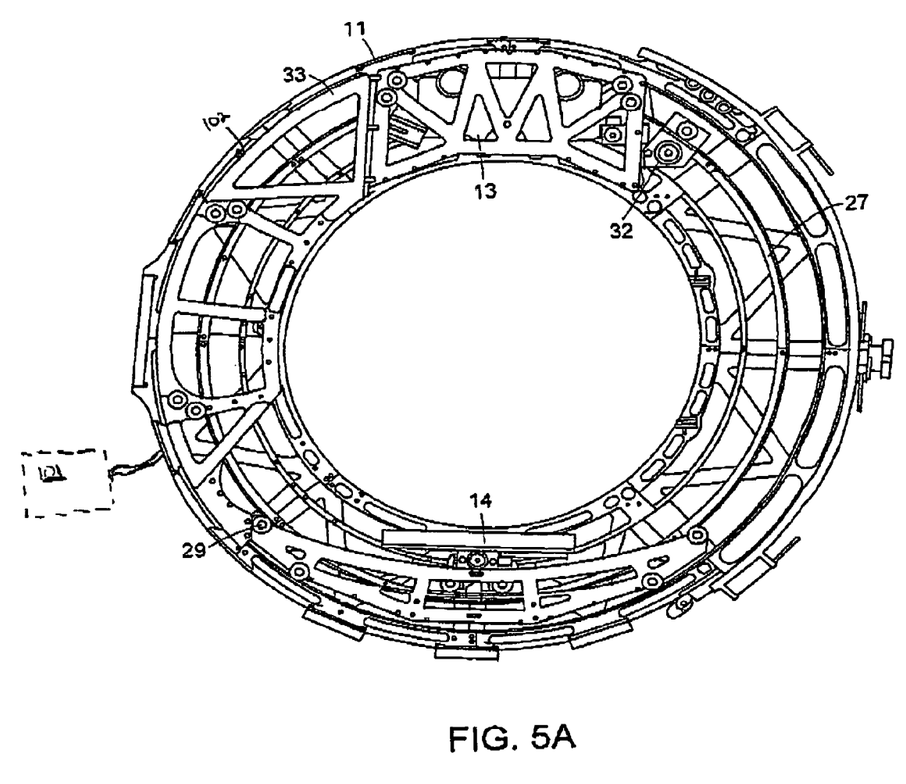
FIG. 5A is a cutaway side view of a gantry ring having a motorized rotor assembly mounted inside the ring.
Figure 5B:
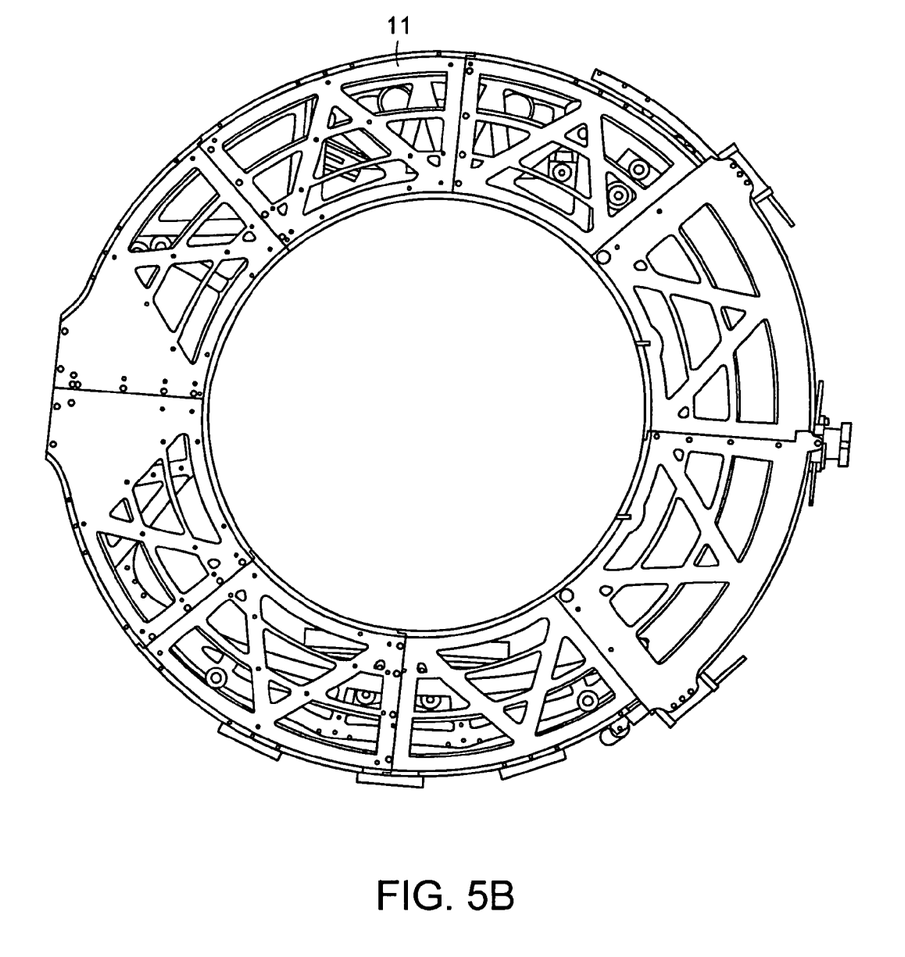
FIG. 5B is a side view of a gantry ring enclosing a motorized rotor assembly.

As shown in FIG. 1, the x-ray source 13 and detector array 14 can be secured to a C-shaped motorized rotor assembly 33. The rigid rotor assembly maintains the source and detector opposed to one another while The entire rotor assembly rotates inside the gantry. As shown in FIGS. 4 and 5A, the rotor assembly 33 also includes a motor 31 and drive wheel 32 for driving the rotor assembly around the interior of the gantry. As shown in FIG. 5A, the interior side walls of the gantry include curved rails 27 extending in a continuous loop around the interior of the gantry. The drive wheel 32 of the rotor assembly 33 contacts the curved rail 27 of the gantry, and uses the tall to drive the rotor assembly around the interior of the gantry. A rotary incremental encoder can be used to precisely measure the angular position of the rotor assembly within the gantry. The incremental encoder van be driven by a friction wheel that tolls on a concentric rail located within the sidewall of the gantry. The rotor assembly 33 also includes bearings 29, which mate with the curved rails 27 of the gantry to help guide the rotor assembly 33 as it rotates inside the gantry. The interior of the gantry ring 11 can include a slip ring 102 that maintains electrical contact with the rotor assembly 33 to provide the power (e.g., from external power source 101) needed to operate the x-ray source/detector and to rotate the entire assembly within the gantry frame. The slip ring can also be used to transmit control signals to the rotor, and x-ray imaging data from the detector to a separate processing unit located outside the gantry, such as the mobile can 12 of FIG. 1. Any or all of the functions of the slip ring could be performed by other means, such as the cable management system described below.

Although the rotor assembly of the preferred embodiment is a C-shaped rotor, it will be understood that other rotor configurations, such as O-shaped rotors, could also be employed. In addition, the x-ray source and detector could rotate independently of one another using separate mechanized systems. Moreover, the x-ray source alone can rotate, with multiple detector arrays located at fixed positions around the interior of the gantry.

The detector array 14 shown in FIG. 4 comprises a two-dimensional flat panel solid-state detector array. It will be understood, however, that various detectors and detector arrays can be used in this invention, including any detector configurations used in typical diagnostic fan-beam or cone-beam imaging systems, such as C-arm fluoroscopes. A preferred detector is a two-dimensional thin-film transistor x-ray detector using scintillator amorphous-silicon technology.

For large field-of-view imaging, the detector 14 can be translated to, and acquire imaging data at, two or more positions along a line or arc opposite the x-ray source 13, such as via a motorized detector rail and bearing system. Examples of such detector systems are described in commonly owned U.S. Provisional Application No. 60/366,062, filed Mar. 19, 2002, the entire teachings of which are incorporated herein by reference.

FIGS. 6A–E illustrate another embodiment of an x-ray imaging apparatus having a cable management system for rotating an x-ray source and detector array 360° around the interior of the gantry ring. In this embodiment, the power for the x-ray source/detector system, as well as for rotating the x-ray source/detector within the gantry, is provided (at least in part) by a cable harness 36 containing one or more cables. The cable harness 36 can also be used to transmit signals and data between the x-ray source/detector and an external processing unit.

Figure 6A:
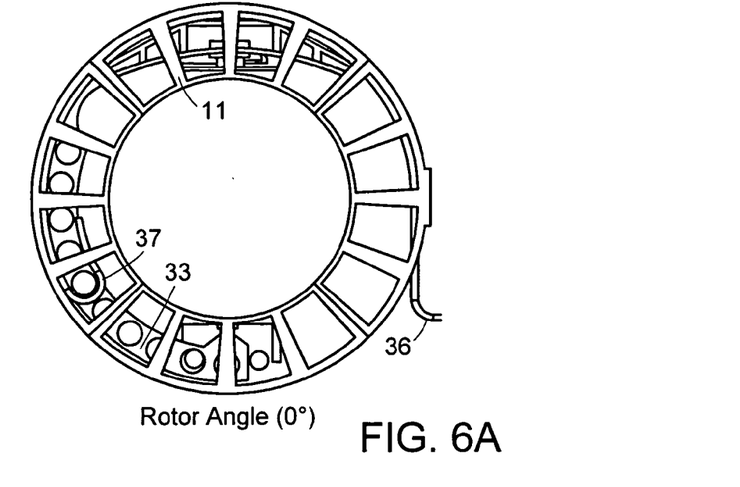
FIGS. 6A–6E illustrate an x-ray imaging apparatus having a cable management system for rotating an x-ray source and detector array around the interior of the gantry ring.
Figures 6B, 6C:
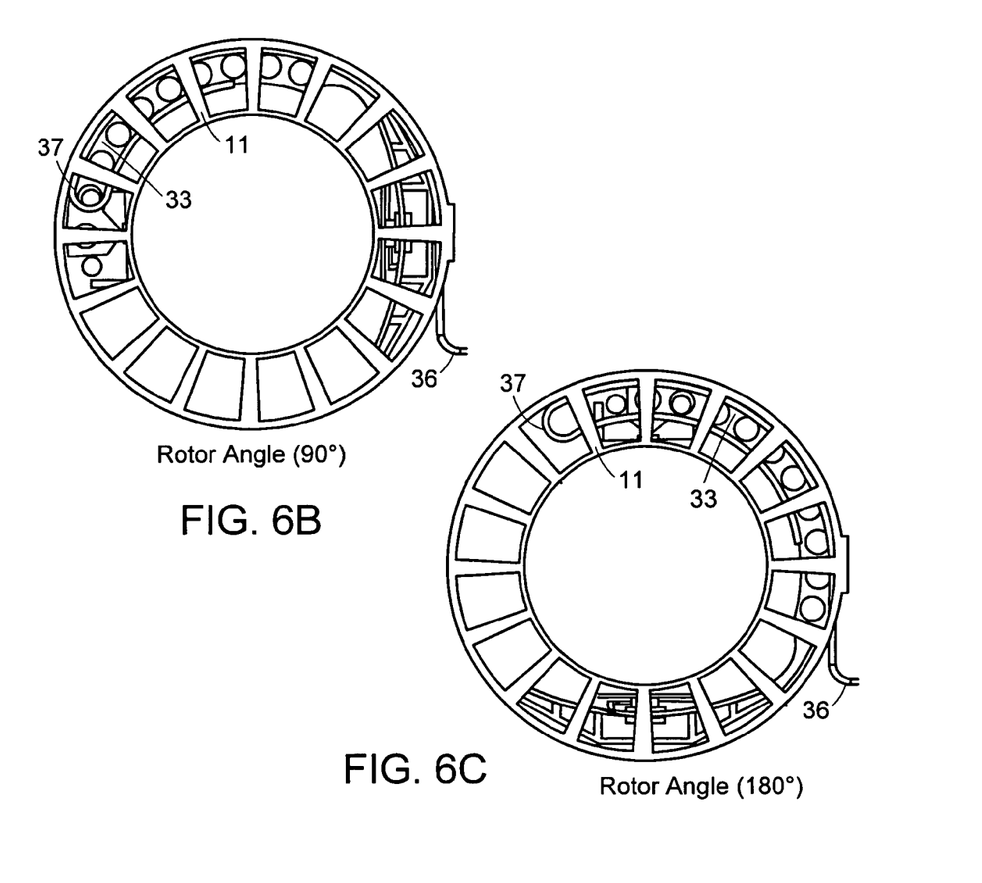
Figure 6D:
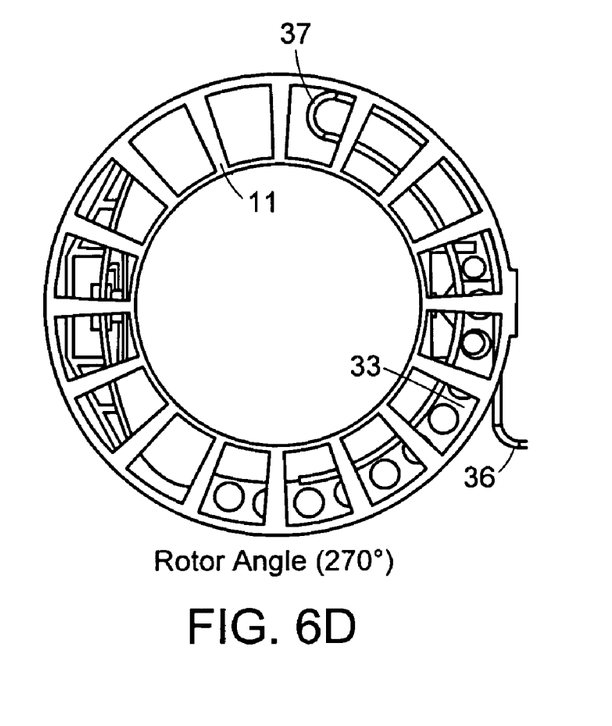
Figure 6E:
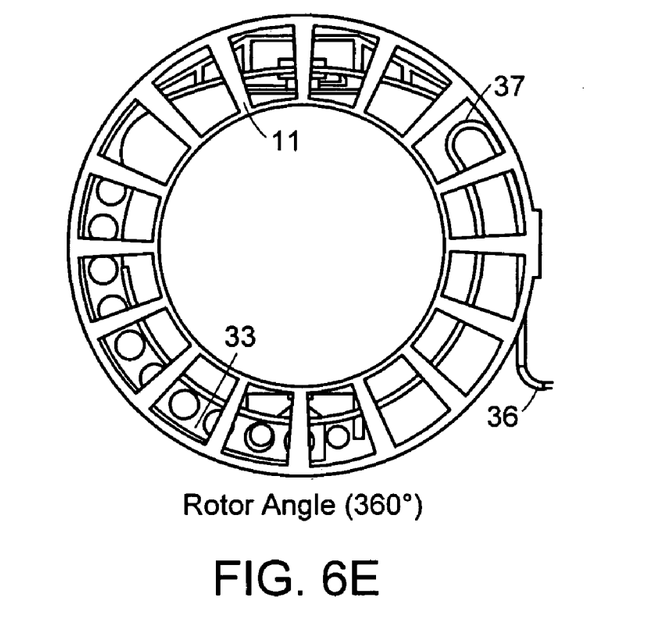

The cable harness 36 is preferably housed in a flexible, linked cable carrier 37. One end of the carrier 37 is fixed to a stationary object, such as the gantry 11 or the cart. The other end of the carrier 37 is attached to the motorized rotor assembly 33 which contains the x-ray source 13 and detector 14. In the example shown in FIGS. 6A–E, the rotor 33 starts at an initial position with the x-ray source 13 at the bottom of the gantry and the detector 14 at the top of the gantry (i.e. rotor angle=0°) as shown in FIG. 6A. The rotor 33 then rotates in a clockwise direction around the interior of the gantry, as illustrated in FIG. 6B (90° rotation), FIG. 6C (180° rotation), FIG. 6D (270° rotation), and FIG. 6E (360° rotation). In FIG. 6E, the rotor 33 has made a full 360° rotation around the interior of the gantry 11, and the rotor is again at the initial position with the x-ray source 13 at the bottom of the gantry, and the detector 14 at the top of the gantry. During the rotation, the cable carrier 37 remains connected to both the rotor 33 and gantry 11, and has sufficient length and flexibility to permit the rotor 33 to easily rotate at least 360° from the start position. To perform another 360° rotation, the rotor 33 can rotate counterclockwise from the end position of the prior rotation (e.g. rotor angle=360° in FIG. 6E) until the rotor 33 returns to the initial position of FIG. 6A. For continuous rotation, this process can repeat itself indefinitely with the rotor making full 360° rotations in alternatively clockwise and counterclockwise directions.

Figure 7:
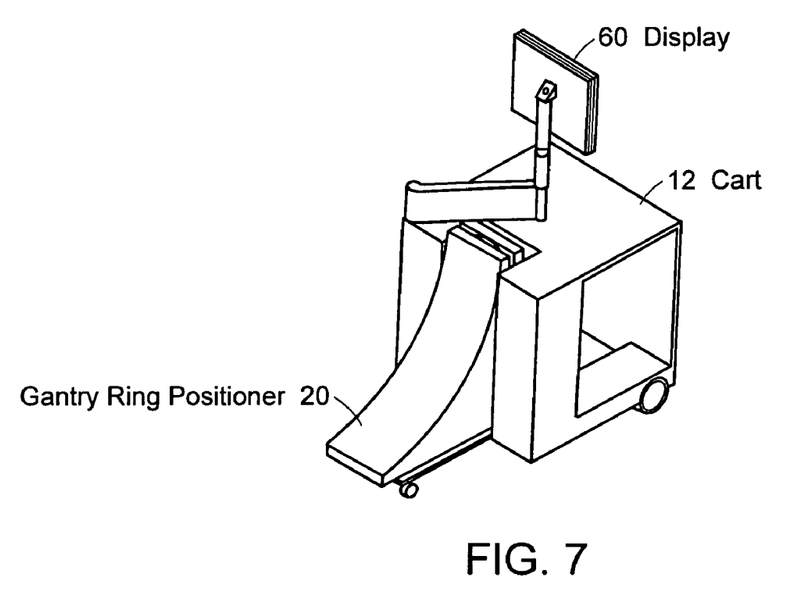
FIG. 7 shows a gantry ring positioning unit in a parked mode.
Figure 8:
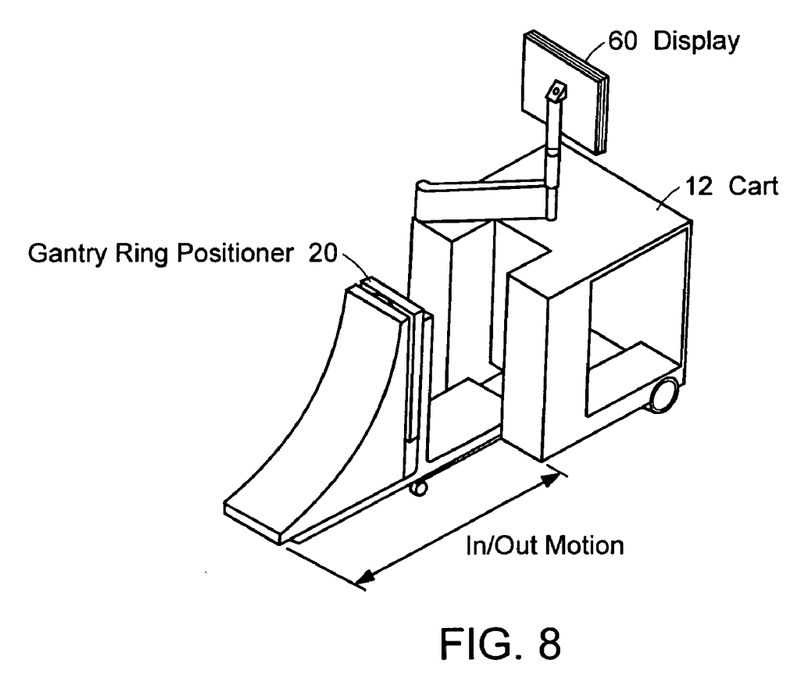
FIG. 8 shows the gantry ring positioning unit in a fully extended lateral position.
Figure 9:
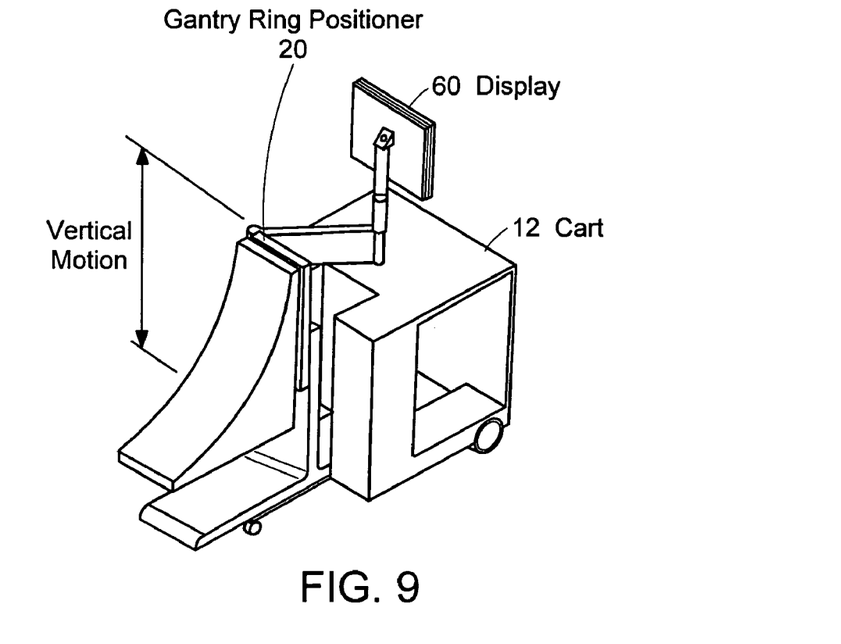
FIG. 9 shows the gantry ring positioning unit in a fully extended vertical position.
Figure 10:
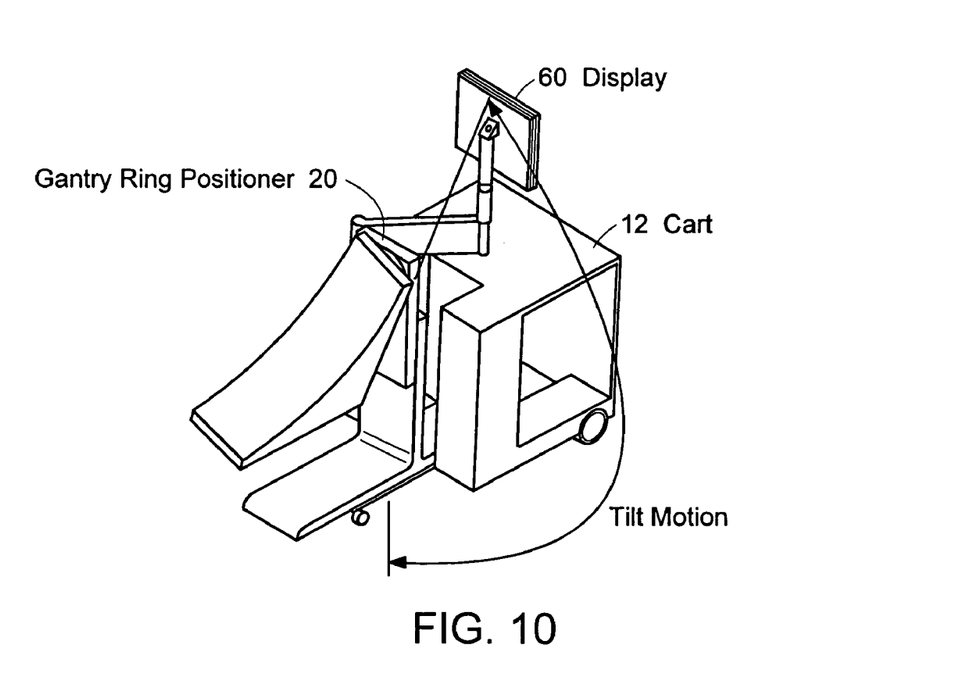
FIG. 10 shows the gantry ring positioning unit in a fully extended tilt position.

As shown in FIGS. 7–11, the ring positioning unit 20 preferably enables the gantry 11 to translate and/or tilt with respect to the support structure. FIG. 7 shows a gantry ring positioning unit in a parked mode. FIG. 8 shows the translational motion of the positioning unit in a lateral direction relative to the cart. FIG. 9 shows translational movement of the positioning unit in a vertical direction relative to the cart. FIG. 10 shows the tilting motion of the positioning unit relative to the cart. In FIG. 11, the entire gantry assembly is illustrated in fully extended lateral, vertical, and tilt positions. The ability of the gantry to translate and tilt in multiple directions allows for the acquisition of x-ray images in any desired projection plane, without having to continuously reposition the patient or the system. As discussed above, a control system can automatically move the gantry to a desired position or orientation, including to user-defined positions and orientations stored in computer memory, for x-ray imaging procedures. X-ray scanning devices with cantilevered, multiple-degree-of-freedom movable gantries are described in commonly owned U.S. Provisional Application No. 60/388,063, filed Jun. 11, 2002, and U.S. Provisional Application No. 60/405,098, filed Aug. 21, 2002, the entire teachings of which are incorporated herein by reference.

Figure 12:
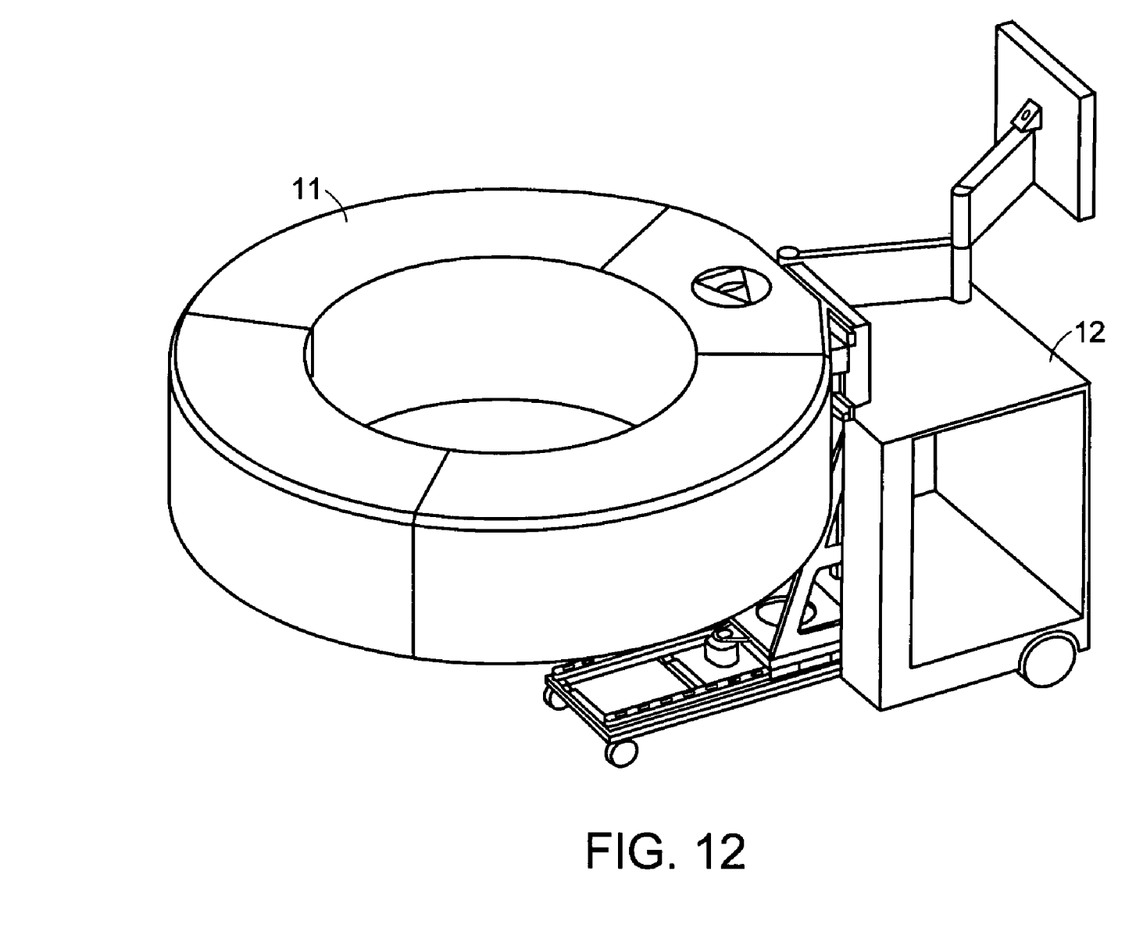
FIG. 12 illustrates an x-ray imaging apparatus having a vertical-axis gantry for imaging a standing or sitting patient.

In the embodiments shown and described thus far, the central axis of the gantry is oriented essentially horizontally, so that an object being imaged, such as a patient, lies lengthwise in the imaging area. In other embodiments, however, the gantry may be aligned so that its central axis extends at virtually any angle relative to the patient or object being imaged. For instance, the central axis of the gantry can be aligned essentially vertically, as shown in FIG. 12. Here, the central opening of the gantry is concentric with the "cylinder" formed by the torso of a standing or sitting human. The entire imaging procedure can thus be performed while the patient remains in a standing or sitting position. Also, in addition to the medical procedures described, the vertical axis gantry may be useful for imaging other objects in which it is convenient to image the object while it is aligned in a standing or vertical orientation.

An imaging device of the present invention could also comprise a substantially O-shaped gantry that includes a segment that at least partially detaches from the gantry ring to provide an opening or "break" in the gantry ring through which the object to be imaged may enter and exit the central imaging area of the gantry ring in a radial direction. An advantage of this type of device is the ability to manipulate the x-ray gantry around the target object, such as a patient, and then close the gantry around the object, causing minimal disruption to the object, in order to perform x-ray imaging. Examples of "breakable" gantry devices for x-ray imaging are described in commonly-owned U.S. patent application Ser. No. 10/319,407, filed Dec. 12, 2002, the entire teachings of which are incorporated herein by reference.

It will also be understood that although the embodiments shown here include x-ray imaging devices having O-shaped gantries, other gantry configurations could be employed, including broken ring shaped gantries having less than full 360 degree rotational capability.

While this invention has been particularly shown and described with references to preferred embodiments thereof, it will be understood by those skilled in the art that various changes in form and details may be made therein without departing from the scope of the invention encompassed by the appended claims.

For instance, although the particular embodiments shown and described herein relate in general to x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

What is claimed is:

1. An imaging apparatus, comprising:
   a substantially O-shaped gantry ring having a central opening for positioning around an object to be imaged, the gantry ring having an interior cavity extending 360 degrees around the interior of the gantry ring;
   a rigid rotor housed within, and rotatable 360 degrees around, the interior cavity of the gantry ring;
   a source of x-ray radiation secured to the rotor at a first position, the source projecting x-ray radiation onto said object from a plurality of different projection angles over a 360 degree rotation of the rotor;
   a detector system, secured to a rotor at a second position, opposite the source on the gantry ring, and detecting the radiation at each projection angle to acquire object images, the imaging apparatus acquiring a series of object images from user-specified non-contiguous projection planes in rapid succession; and
a display that displays each object image as the image is acquired.

2. The apparatus of claim 1, further comprising a motor for rotating the rotor around the interior of the gantry.

3. The apparatus of claim 2, wherein the motor is coupled to an external power source.

4. The apparatus of claim 3, wherein the motor is coupled to an external power source via a slip ring.

5. The apparatus of claim 3, wherein the motor is coupled to an external power source via a cable.

6. The apparatus of claim 1, further comprising a bearing system for guiding the rotation of the rotor around the interior of the gantry.

7. The apparatus of claim 1, wherein the gantry is secured to a mobile support structure.

8. The apparatus of claim 7, wherein the mobile support structure comprises a cart.

9. The apparatus of claim 1, wherein the gantry is secured to a support structure in a cantilevered fashion.

10. The apparatus of claim 1, wherein the gantry is secured to a support structure in a non-cantilevered fashion.

11. The apparatus of claim 1, wherein the gantry can be translated along or rotated around at least one axis, and wherein the rotation of the source is independent of the movement of the gantry.

12. The apparatus of claim 11, comprising a positioning unit for translating and/or tilting the gantry.

13. The apparatus of claim 12, further comprising a control system which directs the positioning unit to move the gantry to a user-defined position and orientation.

14. The apparatus of claim 13, wherein the control system directs the positioning unit based upon stored positioning information.

15. The gantry apparatus of claim 1, wherein the object to be imaged comprises a human patient.

16. The apparatus of claim 1, wherein the rotor is substantially C-shaped.

17. The apparatus of claim 1, wherein the rotor is substantially O-shaped.

18. The apparatus of claim 1, further comprising:
a rotor positioning system to determine the rotational position of the rotor within the gantry ring; and
a drive mechanism secured to the rotor, and adapted to rotate the rotor around the interior of the gantry ring in both a clockwise and a counterclockwise direction.

19. A method of obtaining quasi-simultaneous multi-planar object images using radiation, comprising:
positioning an object within a central opening of a substantially O-shaped gantry ring, the gantry ring having an interior cavity extending 360 degrees around the interior of the gantry ring;
rotating a rigid rotor within the interior cavity of the gantry ring substantially continuously to plural selected rotational positions over the full 360 degree circumference of the gantry, the rotor having a radiation source and a detector secured to the rotor at opposite sides of the gantry ring;
at a plurality of selected, non-contiguous rotational positions of the rotor, projecting x-ray radiation from the source onto the object, and detecting the radiation from the object to acquire object images for multiple projection planes in rapid succession; and
displaying each object image as the image is obtained.

20. The method of claim 19, wherein the object being imaged comprises a human patient.

21. The method of claim 19, further comprising moving the gantry along or around an axis, where the movement of the gantry is independent of the rotation of the source.

22. The method of claim 19, further comprising acquiring object images while continuously rotating the source and detector array on the rotor.

23. The method of claim 19, further comprising displaying object images from multiple projection planes simultaneously.

24. The method of claim 19, further comprising continuously rotating the source to pre-determined projection angles to acquire object images from pre-determined projection planes, and displaying the most recent object image from at least one projection plane.

25. The method of claim 19, further comprising acquiring multiple object images in rapid succession and displaying the images cinematically.

26. The method of claim 19, wherein the projection planes include at least one of anterior, posterior, and lateral projection planes.

27. An imaging apparatus, comprising:
gantry means having an interior cavity extending 360 degrees around the interior of the gantry means for positioning around an object to be imaged;
rotor means rotatable 360 degrees around the interior cavity of the gantry means; radiation means mounted to the rotor means for projecting x-ray radiation onto said object at a plurality of projection angles;
detector means mounted to the rotor means opposite The radiation means for detecting radiation from the object at each projection angle to acquire object images;
the imaging apparatus acquiring a series of object images from user-specified, non-contiguous projection planes in rapid succession; and
display means for displaying each object image as the image is acquired.

28. The apparatus of claim 27, wherein the gantry means is a substantially O-shaped gantry having a central opening for positioning an object to be imaged.

29. The apparatus of claim 27, wherein detector means comprises a detector array rotatable 360 degrees around the interior of the gantry means in coordination with the rotation of the radiation means.

30. The apparatus of claim 27, wherein the radiation means comprises an x-ray source.

31. An imaging apparatus, comprising:
a substantially O-shaped gantry ring having a central opening for positioning around an object to be imaged, the gantry ring having an interior cavity extending 360 degrees around the interior of the gantry ring;
a rigid rotor housed within, and rotatable 360 degrees around, the interior cavity of the gantry ring;
a source of x-ray radiation secured to the rotor at a first position, the source projection x-ray radiation onto said object from a plurality of different projection angles over a 360 degree rotation of the rotor;
a detector system, secured to a rotor at a second position, opposite the source on the gantry ring, detecting the radiation at each projection angle to acquire object images from multiple projection planes in rapid succession;
a rotor positioning system to determine the rotational position of the rotor within the gantry ring;
a drive mechanism that rotates the rotor around the interior of the gantry ring in both a clockwise and a counterclockwise direction; and a control system that receives positioning information from the rotor positioning system, and controls the drive mechanism to rotate the rotor substantially continuously to plural selected rotational positions over the full 360 degree circumference of the gantry, the source and detector acquiring a series of object images from user-specified, non-contiguous projection planes in rapid succession.

32. An imaging apparatus, comprising:
  a substantially O-shaped gantry ring having a central opening for positioning around an object to be imaged, the gantry ring having an interior cavity extending 360 degrees around the interior of the gantry ring;
  a rigid rotor housed within, and rotatable 360 degrees around, the interior cavity of the gantry ring;
  a drive mechanism that rotates the rotor around the interior of the gantry ring in both a clockwise and a counterclockwise direction;
  a source of x-ray radiation secured to the rotor at a first position, the source projecting x-ray radiation onto said object from a plurality of different projection angles over a 360 degree rotation of the rotor; and
  a detector system, secured to a rotor at a second position, opposite the source on the gantry ring, and detecting the radiation at each projection angle to acquire object images, the imaging apparatus acquiring a series of object images from user-specified, non-contiguous projection planes in rapid succession.

33. A method of obtaining quasi-simultaneous multi-planar object images using radiation, comprising:
  positioning an object within a central opening of a substantially O-shaped gantry ring, the gantry ring having an interior cavity extending 360 degrees around the interior of the gantry ring;
  rotating a rigid substantially C-shaped rotor within the interior cavity of the gantry ring substantially continuously to plural selected rotational positions over the full 360 degree circumference of the gantry, the rotor having an x-ray radiation source and a detector secured to the rotor at apposite sides of the gantry ring;
  at each of the selected rotational positions of the rotor, projecting x-ray radiation from the source onto the object and detecting the radiation from the object to acquire object images for multiple projection planes in rapid succession; and
  displaying a plurality of object images sequentially in a cinematic mode.

* * * * *